United States Patent
Xie et al.

(10) Patent No.: US 7,583,821 B2
(45) Date of Patent: Sep. 1, 2009

(54) APPARATUS FOR CLASSIFYING A MATERIAL BY ANALYZING THE MATERIAL'S SURFACE, AND RELATED SYSTEMS AND METHOD

(75) Inventors: Tong Xie, San Jose, CA (US); Marshall Thomas DePue, San Jose, CA (US)

(73) Assignee: Avago Technologies ECBU IP (Singapore) Pte. Ltd., Singapore (SG)

( * ) Notice: Subject to any disclaimer, the term of this patent is extended or adjusted under 35 U.S.C. 154(b) by 899 days.

(21) Appl. No.: 11/019,603

(22) Filed: Dec. 21, 2004

(65) Prior Publication Data

US 2006/0133650 A1    Jun. 22, 2006

(51) Int. Cl.
*G06K 9/00* (2006.01)
*G01N 21/00* (2006.01)

(52) U.S. Cl. .............. 382/108; 382/140; 356/237.5

(58) Field of Classification Search .......... 382/100, 382/103, 106, 108, 111–113, 135–141, 144, 382/168, 148–149, 175, 181, 188, 191, 194, 382/199, 224, 232, 276, 282, 286, 305, 312, 382/318; 356/71, 124, 237.5; 430/108.3
See application file for complete search history.

(56) References Cited

U.S. PATENT DOCUMENTS

| | | | |
|---|---|---|---|
| 4,724,322 A | 2/1988 | Knowles et al. | |
| 6,189,991 B1 | 2/2001 | Wen | |
| 6,496,253 B1 * | 12/2002 | Vokhmin | 356/124 |
| 7,068,363 B2 * | 6/2006 | Bevis et al. | 356/237.5 |
| 7,155,052 B2 * | 12/2006 | Geshel et al. | 382/144 |
| 7,218,386 B2 * | 5/2007 | Alcock et al. | 356/71 |
| 7,232,202 B2 | 6/2007 | Kinpara | |
| 7,320,850 B2 * | 1/2008 | Itakura et al. | 430/108.3 |
| 2004/0246290 A1 | 12/2004 | Hayashi et al. | |
| 2004/0246476 A1 * | 12/2004 | Bevis et al. | 356/237.5 |

* cited by examiner

*Primary Examiner*—Seyed Azarian

(57) ABSTRACT

An apparatus classifies a material, which may include identifying the material, identifying the type of the material, or identifying the type of the material's surface. The apparatus includes a detector for capturing an image of a surface of the material, and a processor classifies the material by analyzing the image. When incorporated in a mechanism, this apparatus can classify the material on which the mechanism is operating, and, thus, the mechanism can tune some or all of its settings to the material without inconvenience to and with no susceptibility to error by a human operator. For example, when incorporated in a printer, this apparatus can identify the type of media being printed, and, thus, the printer can tune its print settings to the identified media type without relying on operator input.

14 Claims, 7 Drawing Sheets

APPARATUS FOR CLASSIFYING A MATERIAL BY ANALYZING THE MATERIAL'S SURFACE, AND RELATED SYSTEMS AND METHOD

CROSS-REFERENCE TO RELATED APPLICATION

This application is related to commonly owned U.S. patent application Ser. No. 11/019,605 entitled, which was filed on the same day as the present application and which is incorporated by reference.

BACKGROUND OF THE INVENTION

For a mechanism that can operate on different materials, it may be desired that the mechanism have settings that are adjustable, i.e., tunable, to the characteristics of a particular material so that the mechanism performs better on that material. For example, it is often desired that the suction of a vacuum cleaner be tunable to the type of material being cleaned, e.g., weaker suction for drapes and stronger suction for carpets. And it is often desirable that the settings of a printer be tunable according to the type of medium being printed, e.g., heavier ink/toner for bond paper and lighter ink/toner for photo (glossy) paper.

Unfortunately, some of today's mechanisms have few or no settings that are tunable to materials on which the mechanisms operate. For example, a computer navigation device typically has no settings that are tunable to the type of surface (e.g., smooth, rough, fibrous) on which the navigation device is disposed and over which an operator navigates the navigation device.

And although other of today's mechanisms have settings that are tunable to materials on which the mechanisms operate, the tuning of these settings may be inconvenient or susceptible to operator error. For example, a printer may include a keypad and a display screen that allow an operator to identify the type of paper in the printer before running a print job. But this technique for tuning the printer settings may inconvenience the operator, and is susceptible to the operator identifying the incorrect type of paper. Alternatively, a printer may have one or more trays that can each hold a different type of paper, and may allow an operator to identify the type of paper in each tray. Although this technique may be more convenient than the former technique because the operator need not identify the type of paper before each print job, it is still susceptible to the operator erroneously loading a tray with an incorrect type of paper.

SUMMARY OF THE INVENTION

An aspect of the invention is an apparatus for classifying a material, which includes, for example, identifying the material (e.g., wood, carpet, bond paper, photo paper), identifying the type of material (e.g., hard, soft), or identifying the type of the material's surface (e.g., smooth, rough). The apparatus includes a detector for capturing an image of a surface of the material, and a processor classifies the material by analyzing the image.

When incorporated in a mechanism, this apparatus can classify the material on which the mechanism is operating, and, thus, the mechanism can tune some or all of its settings to the characteristics of the classified material without inconvenience to and with no susceptibility to error by a human operator. For example, when incorporated in a printer, this apparatus can identify the type of media being printed, and, thus, the printer can tune its print settings to the identified media type without relying on operator input. Or, when incorporated in a computer navigation device, this apparatus can identify the type of surface on which the navigation device is disposed, and, thus, the navigation device can tune its appearance, performance, and other settings to the identified surface type.

BRIEF DESCRIPTION OF THE DRAWINGS

The foregoing aspects and many of the attendant advantages of this invention will become more readily appreciated as the same become better understood by reference to the following detailed description in conjunction with the accompanying drawings.

DETAILED DESCRIPTION

The following discussion is presented to enable a person skilled in the art to make and use the invention. The general principles described herein may be applied to embodiments and applications other than those detailed below without departing from the spirit and scope of the invention. Therefore the invention is not intended to be limited to the embodiments shown, but is to be accorded the widest scope consistent with the principles and features disclosed or suggested herein.

Figure 1:
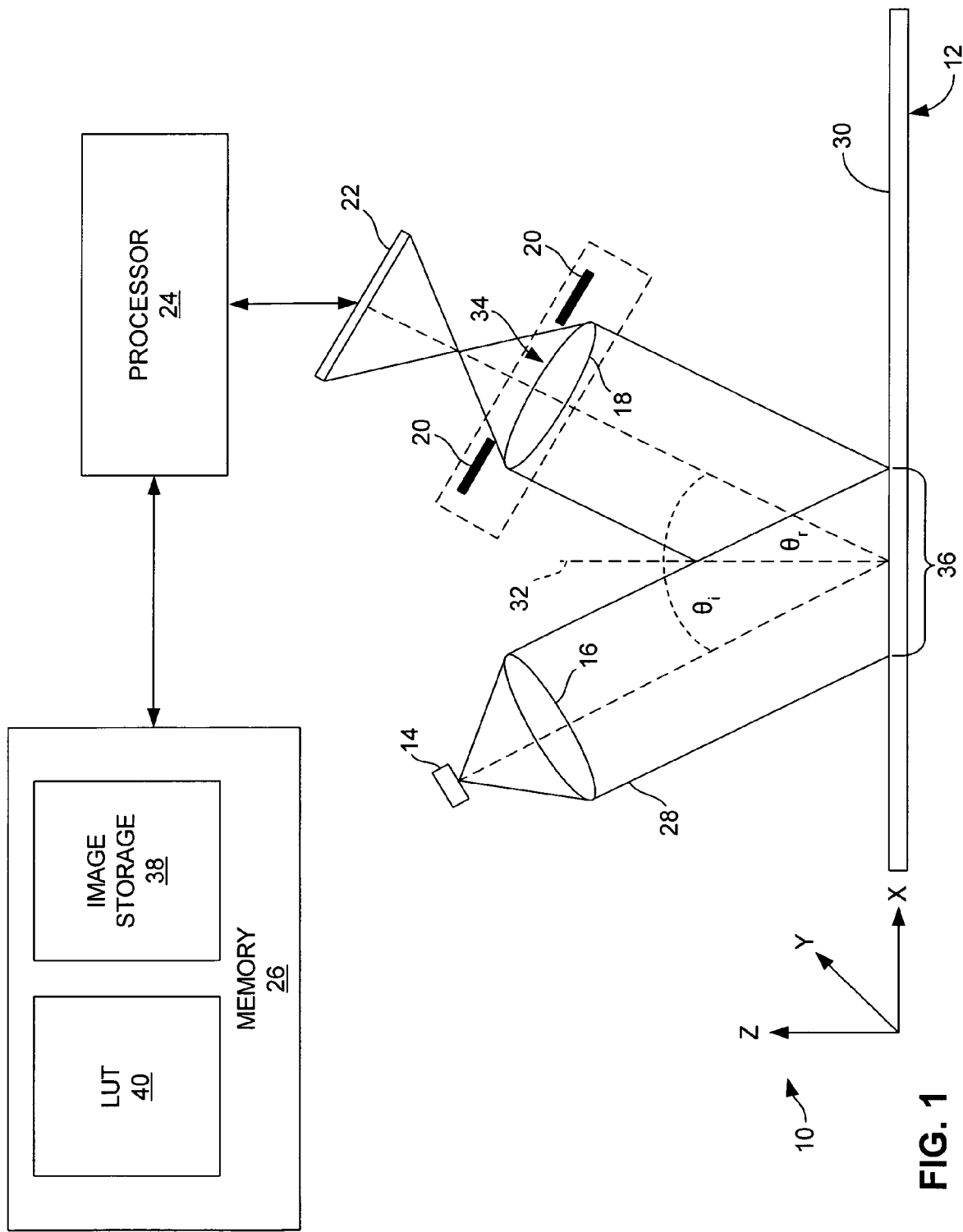
FIG. 1 is a diagram of an apparatus that can classify a material according to an embodiment of the invention.

FIG. 1 is a diagram of a material classifier, i.e., a material-classifying apparatus 10, that can classify a material 12 according to an embodiment of the invention. That is, the apparatus 10 can determine characteristics of the material, such as the identity of the material (e.g., wood, carpet), the type of material (e.g., hard, soft), or the type of the material's surface (e.g., smooth, rough). Because this classification is independent of a human operator, the apparatus 10 allows a mechanism that incorporates the apparatus to tune its settings to a classified material without inconvenience to the operator and with little or no susceptibility to an error by the operator.

The apparatus 10 includes a beam source 14, optional collimating optics 16 and collecting optics 18, an optional baffle 20 defining an aperture 34, an image-capture detector 22, a processor 24, and a memory 26. The structure and operation of the apparatus 10 are described below and in commonly owned U.S. patent application Ser. Nos. 10/680,525 filed Oct. 6, 2003, and Ser. No. 10/977,720 filed Oct. 30, 2004, which are incorporated by reference.

The beam source 14 generates a beam 28 of coherent or quasi-coherent light, which strikes a surface 30 of the material 12 at an angle of incidence $\theta_i$ to a line 32 that is normal to the surface. For example, the beam source 14 may be a laser such as a laser diode or vertical-cavity-surface-emitting laser (VCSEL), an light-emitting diode (LED), or combination of light emitting source and optical filter.

The collimating optics 16 shapes the beam 28, and may include a single collimating lens as shown, or may include one or more refractive or diffractive optical elements (not shown). But as discussed above, the collimating optics 16 may be omitted particularly where the beam source 14 can be placed close to the surface 30.

The collecting optics 18 sizes to the full or approximately the full pixel-array area of the image-capture detector 22 a portion of the beam 28 that the surface 30 reflects at an angle of reflectance $\theta_r$ to the normal line 32. Preferably, $\theta_r = \theta_i$. The collecting optics 18, however, may not focus the beam 28 onto the image-capture detector 22; that is, the image that the collecting optics forms on the image-capture detector may be defocused. The collecting optics 18 may include a single imaging lens as shown, or may include one or more refractive or diffractive optical elements (not shown). But, as discussed above, the collecting optics 18 may be omitted, particularly in cases where the optical efficiency of the apparatus 10 is relatively high, which facilitates generation of an image of sufficient brightness on the detector 22.

The baffle 20 prevents ambient light from striking the image-capture detector 22 and corrupting the captured image. Specifically, the baffle 20 defines an aperture 34, which limits the amount of light that strikes the image-capture detector 22. But as discussed above, the baffle 20 may be omitted.

The image-capture detector 22 captures an image by generating respective digital values for the pixels that compose an image of a region 36 of the surface 30. That is, the image-capture detector 22 generates a respective digital value for each pixel, the value corresponding to the brightness, i.e., luminance, of the pixel.

Still referring to the image-capture detector 22, the surface region 36 reflects at least a portion of the beam 28 at an angle $\theta_r$ and onto the detector. Because the beam 28 is coherent or quasi-coherent light, the rays of the reflected beam portion are influenced by the surface 30, and thus form on the detector 22 a pattern characteristic of the surface. Such a pattern may be a laser-speckle pattern having dark regions (regions of destructive interference) and bright regions (regions of constructive interference), a picture of the surface, or a diffraction pattern. As discussed below, these patterns are related to the characteristics of the surface region 36, and thus can be used to classify the material 12. That is, one can use the pattern to, e.g., distinguish one material from another material, one type of material from another type of material, or one type of surface from another type of surface. For example, a smooth surface region 36 causes the reflected portion of the beam 28 to have one pattern, and a rough surface region causes the reflected portion of the beam to have another pattern. Furthermore, patterns generated with coherent or quasi-coherent light typically have high contrast (i.e., the luminance difference between the brightest and darkest pixels is relatively large), and, therefore, may be easier to process than low-contrast patterns. The detector 22 generates the pixels that form the pattern, which effectively is an image of the surface region 36.

Still referring to FIG. 1, the image-capture detector 22 may be any type of conventional image-capture detector such as a CMOS pixel array or a charge-coupled-device (CCD) array. Furthermore, the image-capture detector 22 may have a relatively low resolution, such as a 30×30 array of 30×30 micron pixels.

As discussed in the following paragraphs, the processor 24 analyzes the images captured by the image-capture detector 22 to classify the material 12.

First, the processor 24 stores the pixel values of the captured image in an image-storage section 38 of the memory 26.

Next, the processor 24 analyzes the stored pixel values according to one or more image-processing techniques to determine one or more characteristics of the captured image. For example, as discussed below in conjunction with FIGS. 2A-4B, the processor 24 may generate from the stored pixel values a histogram, which is the distribution of the pixel values within predetermined brightness ranges. Thus, a histogram is a characteristic of the captured image.

Then, the processor 24 effectively compares at least one of the determined characteristics of the captured image to a look-up table (LUT) 40 of like characteristics that have been predetermined for various materials. For example, the LUT 40 may store the histograms of a number of materials and/or surface types.

Next, the processor 24 determines which of the characteristics stored in the LUT 40 is closest to the characteristic of the captured image, and classifies the material 12 with the stored information associated with the closest stored characteristic. For example, the stored information may identify the material, type of material, or type of surface.

Figure 2B:
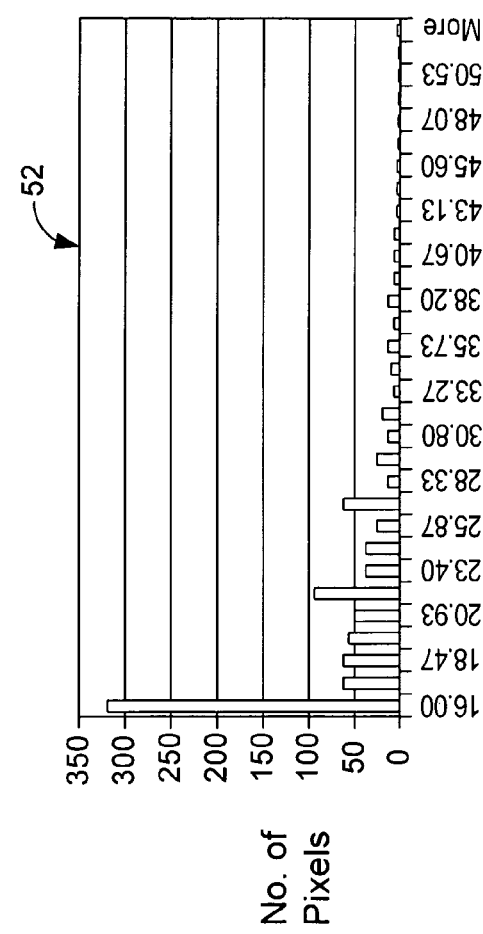
FIG. 2B is a histogram of the image of FIG. 2A generated with the apparatus of FIG. 1 according to an embodiment of the invention.
Figure 2A:
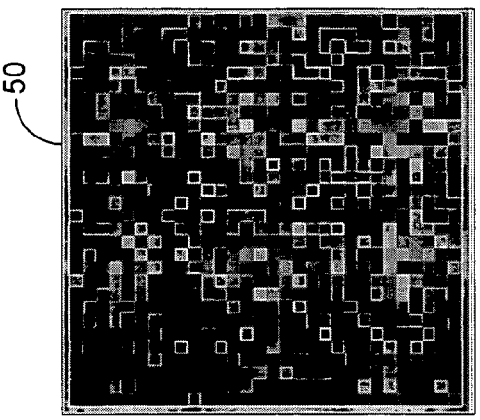
FIG. 2A is an image of a smooth, shiny surface captured with the apparatus of FIG. 1 according to an embodiment of the invention.

FIG. 2A is a 30-×-30-pixel image 50 of a surface region of a white board (not shown), the image having been captured by a detector such as the detector 22.

FIG. 2B is a histogram 52 of the captured image 50 of FIG. 2A. Specifically, the histogram 52 plots the distribution of the luminance values for the pixels in the image 50. The horizontal axis of the histogram 52 indicates luminance level, which increases from left to right, and the vertical axis indicates the number of pixels corresponding to each luminance level or range of brightness levels. According to the histogram 52, approximately ⅓ (~320 out of 30×30=900) of the pixels of the image 50 have luminance values that are less than or equal to a normalized luminance level 16.00, and virtually no pixels have luminance values greater than 33.27. A coherent laser source 14 allows for high-contrast images. Glossy surfaces, such as the shiny white-board surface region upon which the beam 28 is incident, tend to have a relatively peaked distribution as a large fraction of the pixels of the captured image are dark.

Figure 3B:
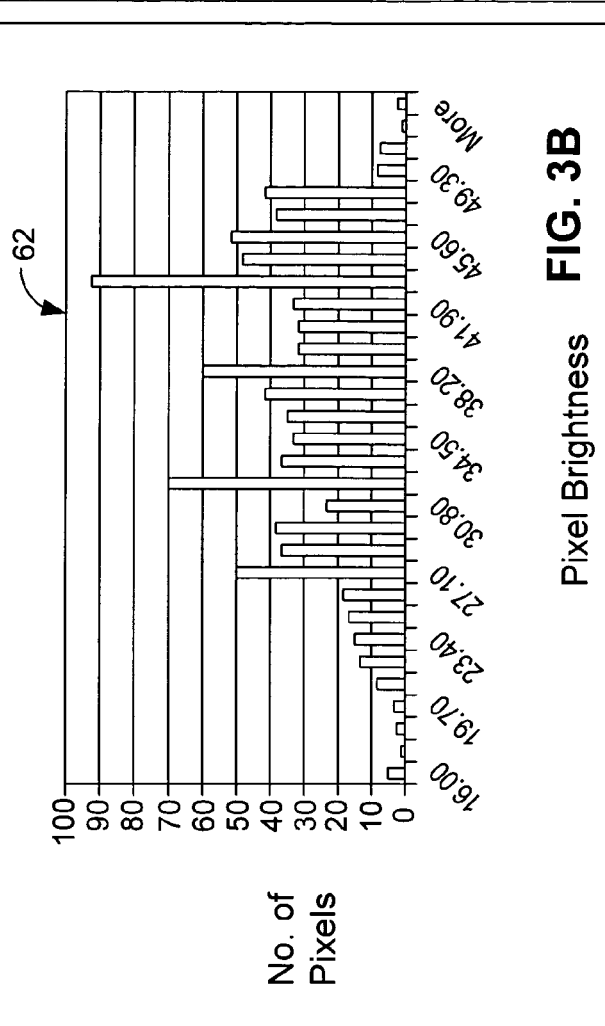
FIG. 3B is a histogram of the image of FIG. 3A generated with the apparatus of FIG. 1 according to an embodiment of the invention.
Figure 3A:
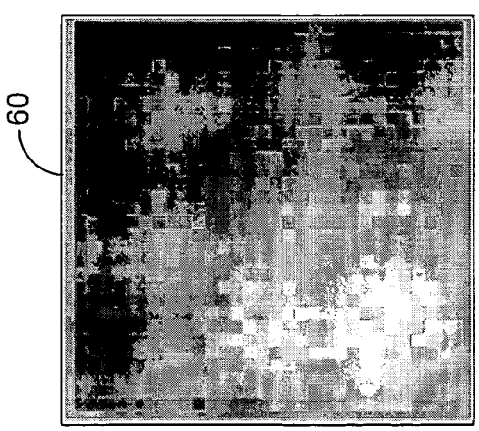
FIG. 3A is an image of a rough surface captured with the apparatus of FIG. 1 according to an embodiment of the invention.

FIG. 3A is a 30-×-30-pixel image 60 of a surface region of a piece of white bond paper (not shown), the image having been captured by a detector such as the detector 22.

FIG. 3B is a histogram 62 of the captured image 60 of FIG. 3A. According to the histogram 62, most of the pixels of the image 60 have luminance values that are between the levels 27.10 and 49.30. It is theorized that the histogram of pixel values has a broad distribution because the rough bond-paper surface (not shown) upon which the beam 28 is incident may be approximated as a Lambertian scatterer.

Figure 4B:
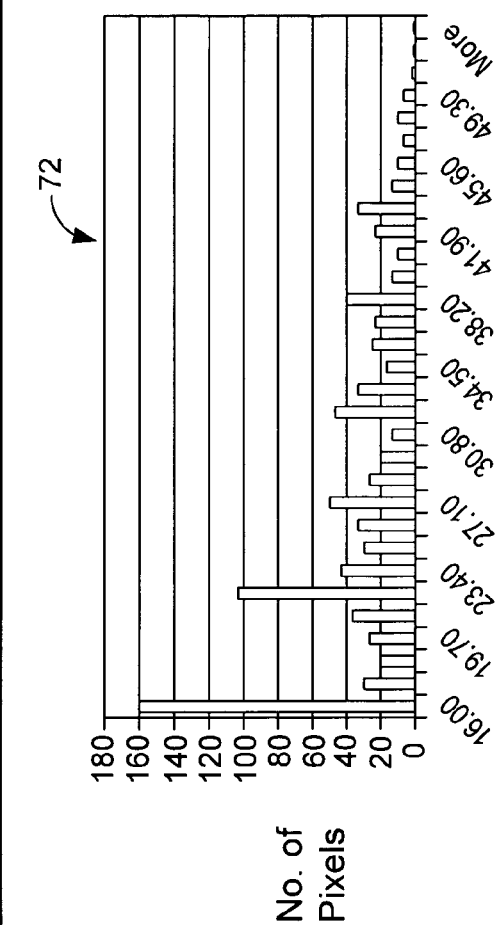
FIG. 4B is a histogram of the image of FIG. 4A generated with the apparatus of FIG. 1 according to an embodiment of the invention.
Figure 4A:
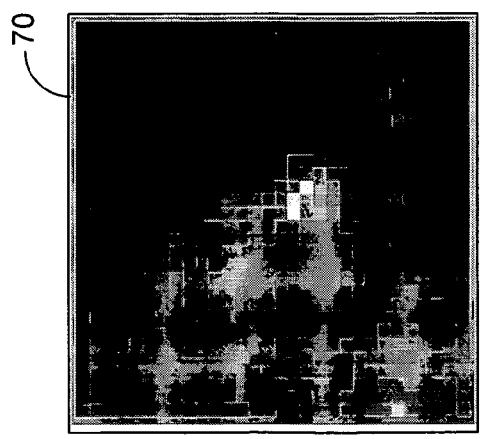
FIG. 4A is an image of a fibrous surface captured with the apparatus of FIG. 1 according to an embodiment of the invention.

FIG. 4A is a 30-×-30-pixel image 70 of a surface region of a carpet (not shown), the image having been captured by a detector such as the detector 22.

FIG. 4B is a histogram 72 of the captured image 70 of FIG. 2A. According to the histogram 72, the although the majority of pixels of the image 70 are relatively dark, the luminance values for these pixels are more evenly distributed than the luminance values for the pixels of the images 50 (FIG. 2A) and 60 (FIG. 3A). It is theorized that the darker pixels of the image 70 result from some of the incident light from the beam 28 being trapped within the cavities created by the carpet fibers or being scattered by the fibers away from the aperture 34, and that the brighter pixels result from some of the incident light being reflected toward the aperture by long strands of fiber.

Referring to FIGS. 1-2B, the operation of the material-classifying apparatus 10 is discussed according to an embodiment of the invention where the material 12 is a white board. The image-capture detector captures the image 50, and the processor 24 generates the histogram 52 of the captured image. It is understood, however, that the operation of the apparatus 10 is similar where the material 12 is another material such as bond paper or carpet.

At some time after the beam source 14 is activated, the collimating optics 16 (if present) directs the beam 28 at an angle of incidence $\theta_i$ onto the surface region 36, which reflects a portion of the beam to the collecting optics 18 (if present) at an angle of reflectance $\theta_r$.

The reflected portion of the beam 28 then propagates through the aperture 34 (if the baffle 20 is present) onto the image-capture detector 22, which captures the image 50 of the surface region 36 and generates luminance values for the pixels that compose the captured image.

Next, the processor 24 generates the histogram 52 of the captured image 50 by processing the pixel luminance values according to a conventional image-processing algorithm. For example, the processor 24 may process the pixel luminance values one row or column at a time.

Then, the processor 24 provides the histogram 52, or parameters that define the histogram, as an input to the LUT 40, which, as discussed above, stores predetermined histograms for materials, types of materials, or types of surfaces. For example, the processor 24 may provide as an input to the LUT 40 the number of pixels having luminance values at each brightness level 16.00, 18.47, . . . , and 50.53. Or, the processor 24 may provide as an input to the LUT 40 the number of pixels having luminance values below or above one or more predetermined brightness thresholds. Alternatively, the processor 24 may provide to the LUT 40 other values or combinations of values derived from the histogram 52.

Next, the LUT 40 returns information that classifies the material 12, e.g., the identity of the material 12 (here a white board), the type of material 12 (here solid), or the type of surface 30 (here a smooth, shiny surface). The LUT 40 is conventionally programmed such that the input from the processor 24 effectively addresses a memory location that stores this classifying information for the material having an image with a histogram that is closest (out of all the histograms programmed into the LUT 40) to the histogram 52.

Referring again to FIG. 1, other operational embodiments of the material-classifying apparatus 10 are contemplated. Instead of computing a histogram of the captured image, the processor 24 may characterize the captured image using other image-processing techniques. For example, the processor 24 may compute a spatial Fourier transform of the image, and compare the computed transform to predetermined transforms stored in the LUT 40 and corresponding to for a number of materials. Alternatively, the processor 24 may compute a histogram of only a portion of the captured image, such as a lone pixel, a single horizontal or vertical line, or other grouping of pixels. Furthermore, the processor 24 may compare a characteristic of the captured image to predetermined like characteristics a number of materials without the LUT 40. For example, the processor 24 may retrieve the predetermined like characteristics from the memory 26 and perform the comparison itself.

Alternate embodiments of the material-classifying apparatus 10 are contemplated. Instead of classifying the material 12 based on a single captured image of the surface 30, the apparatus 10 may base its classification on multiple captured images of the surface. For example, the processor 24 may compute a spatial average multiple captured images, and then compute, e.g., the histogram, spatial Fourier-Transform, or threshold characteristic from the spatial average. Taking the spatial average may improve the signal-to-noise ratio.

Figure 5:
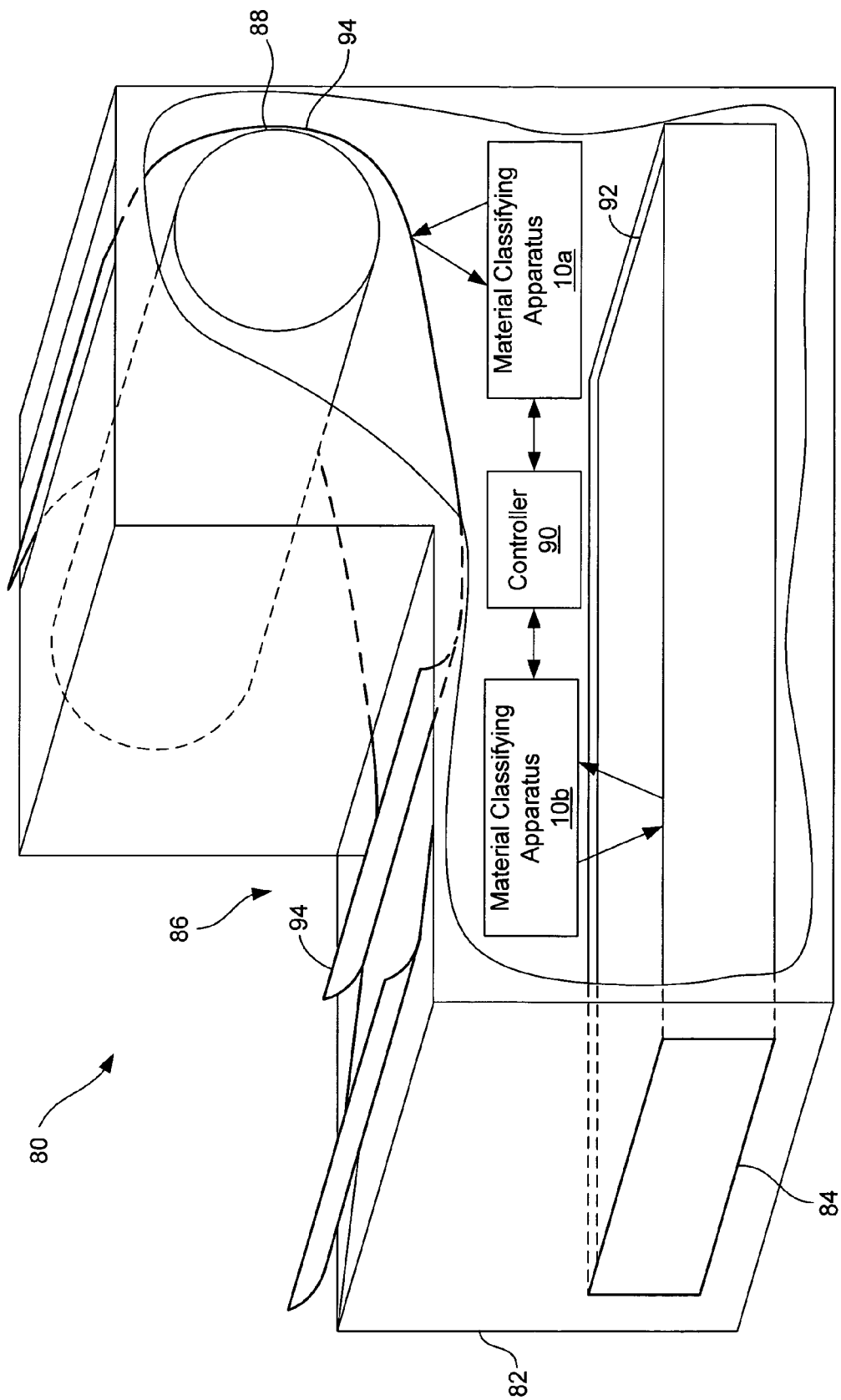
FIG. 5 is an isometric view with portions broken away of a printer that includes the apparatus of FIG. 1 according to an embodiment of the invention.

FIG. 5 is an isometric view with portions broken away of a printer 80 that includes one or more material-classifying apparatuses 10 of FIG. 1 for identifying the type(s) of paper in the printer according to an embodiment the invention.

In addition to apparatuses 10a and 10b, the printer 80 includes a housing 82, a print-media tray 84, a manual print-media feed 86, a roller 88, and a controller 90. The tray 84 can store one or more sheets of media 92, and the manual feed 86 can receive one or more sheets of media 94 independent of the tray 84. The roller 88 advances one sheet of media 92 or 94 at a time from either the tray 84 or manually feed 86 (as shown), respectively, and otherwise assists in the printing of the advancing media. The controller 90 tunes the printing settings and otherwise controls the operations of the printer 80. Examples of the printing settings include, e.g., the font size, the amount of printing agent used per printed character, the length of time between the printing of consecutive lines (this time may be adjusted to prevent smudging by allowing the printing agent to dry before advancing the paper for the printing of the next line), the resolution, the speed, and other feed parameters (e.g., acceleration of the medium). The printer 80 may also include additional components that, for clarity, are omitted from FIG. 5. Furthermore, examples of print media include paper and transparencies, and examples of printing agent include ink and toner.

During a print mode of operation, the controller 90 tunes one or more predetermined settings of the printer 80 based on the type of print media currently being printed (here the media 94).

First, the apparatus 10a identifies the type of media 94 currently being advanced by the roller 88 by capturing and analyzing one or more images of the media surface in a manner similar to that discussed above in conjunction with FIGS. 1-4B. For example, bond paper (which has a rough surface) may generate an image (as captured by the detector 22 of FIG. 1) similar to the image 60 of FIG. 3A and having a histogram similar to the histogram 62 of FIG. 3B, and a transparency (which has a smooth, shiny surface) may generate an image similar to the image 50 of FIG. 2A and having a histogram similar to the histogram 52 of FIG. 2B.

Next, the controller 90 adjusts one or more predetermined print settings according to the type of media 94 identified by the apparatus 10a. For example, suppose that the apparatus 10a identifies the sheet of paper 94 as bond paper. The controller 90 may adjust the amount of ink used per character and the time between the printing of consecutive lines to levels that have been predetermined to be the best levels for bond paper which may require more ink per character than copy paper to account for higher ink absorption, and may require a longer drying time to prevent smudging.

Consequently, the controller 90 can, without operator input, automatically optimize the print settings for the type of media 94 being printed. As a result, the optimization of the print settings is less susceptible to operator error than a conventional printer that lacks the apparatus 10a.

Furthermore, the controller 90 may display the identified type of the media 94 on a screen (not shown) of the printer 80, or otherwise inform the operator (not shown) of the media type so that if the media is of an undesired type, the operator can suspend the print job, change the media to the desired type (or switch to printing the media 92 from the tray 84), and then restart the print job before any media are printed. Without the apparatus 10a, the printer 80 might print one or more pages of the media 94 before the operator realizes that this media is of an undesired type. Consequently, by identifying the media type before commencement of the print job, the controller 90 helps conserve print media by informing the operator of an undesired media type before the printer 80 prints one or more pages that the operator may ultimately discard.

Still referring to FIG. 5, during a standby mode of operation, the apparatus 10b identifies the type of the media 92 currently in the tray 84 by capturing and analyzing one or more images of the media surface in a manner similar to that discussed above in conjunction with FIGS. 1-4B.

Next, the controller 90 may display the type of the media 92 on a screen (not shown) of the printer 80, or otherwise inform the operator (not shown) of the media type so that if the tray is loaded with media of an undesired type, the operator can reload the tray with media of a desired type before commencing a print job. Informing the operator of the type of the media 92 may also conserve media as discussed above.

Still referring to FIG. 5, other embodiments of the printer 80 are contemplated. For example, the printer 80 may omit the apparatus 10b, or may include additional media trays and a respective apparatus 10 positioned to identify the media in each tray. Furthermore, the printer 80 may omit the controller 90, and a computer (not shown in FIG. 5) to which the printer is coupled may perform the controller functions discussed above. In addition, the printer 80 may disable printing until the desired type of media is loaded into the tray 84 or manual feed 86. For example, suppose using a word-processing software application such as MS Word® an operator specifies the type of paper to be used in printing a document. If the controller 90 determines that the specified type of paper is not loaded in the tray 84 or feed 86, then the controller can send an error message to the operator via the software application or a display screen (not shown) on the printer 80. The controller 90 can also suspend printing until the operator loads the specified type of paper into the printer tray 84 or feed 86 or specifies a type of paper that is already in the tray or feed. Moreover, the functions of the controller 90 may be performed by the processor 24 of the apparatus 10a or 10b, or the functions of one or both of the processors 24 of the apparatuses 10a and 10b may be performed by the controller 90.

Figure 6:
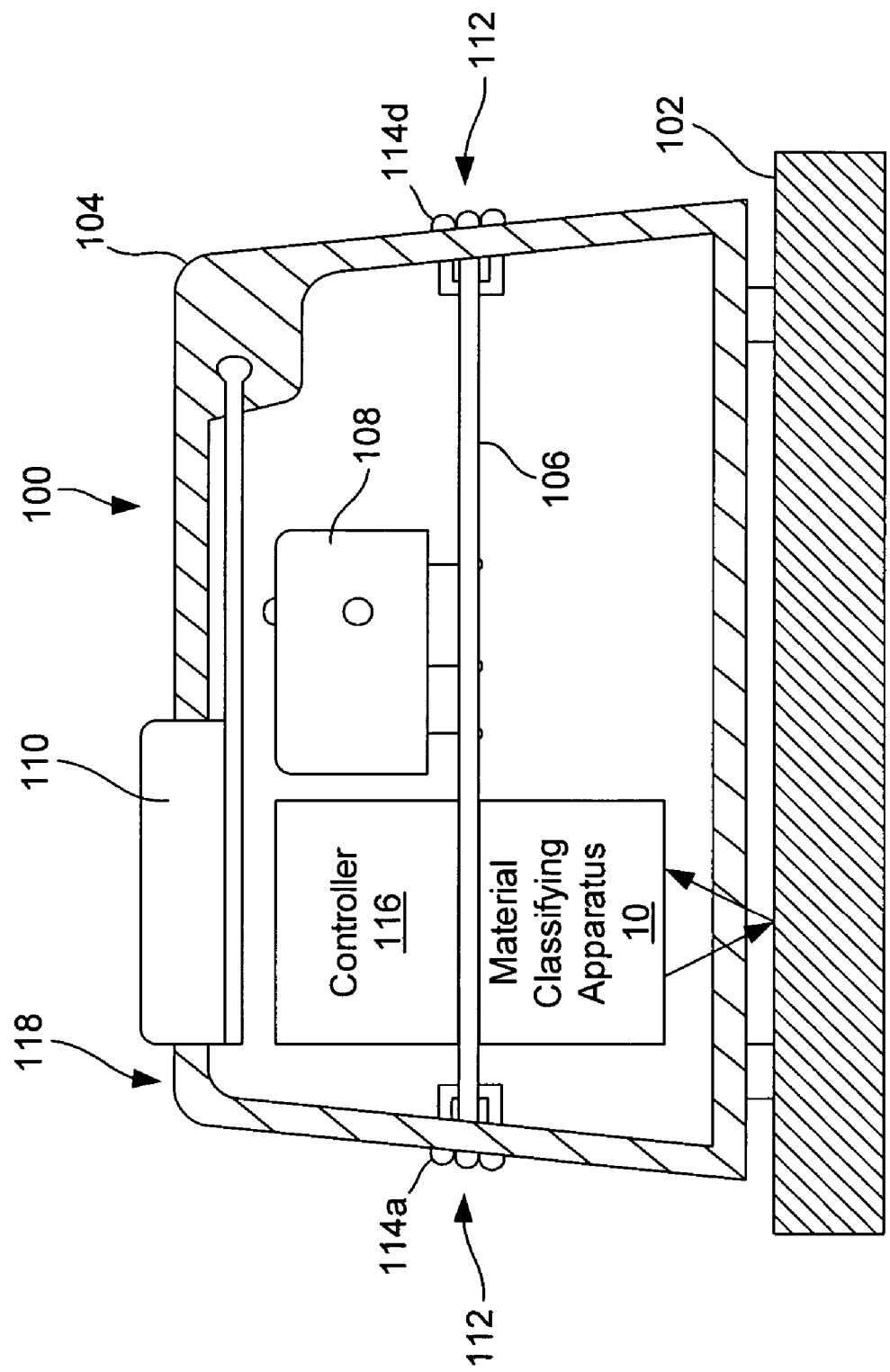
FIG. 6 is a cutaway side view of a computer navigation device that includes the apparatus of FIG. 1 according to an embodiment of the invention.

FIG. 6 is a cut-away side view of a computer mouse, i.e., optical navigation device, 100 that includes one or more material-classifying apparatuses 10 of FIG. 1 for identifying the type of surface 102 that the navigation device is disposed on according to an embodiment the invention.

In addition to the apparatus 10, the navigation device 100 includes a housing 104, a printed circuit board (PCB) 106, a transmitter 108 for wirelessly communicating with a computer (not shown in FIG. 6), one or more clickable buttons 110, an array 112 of LEDs 114 that light in a pattern corresponding to the type of the surface 102 as identified by the apparatus 10, and a controller 116 for controlling the operation of the navigation device. The apparatus 10, transmitter 108, LEDs 114, and controller 116 are mounted to the PCB 106, which has conductive traces (not shown) that enable communication between the apparatus, transmitter, LEDs, and other components that are omitted for clarity. The clickable button 110 allows an operator (not shown) to select items displayed on the computer and is mounted in an opening 118 defined by an upper portion of the housing 104.

During operation of the navigation device 100 according to an embodiment of the invention, the controller 116 tunes one or more predetermined settings of the navigation device based on the type of the surface 102 on which the navigation device is disposed. For example, the controller 116 may cause the LEDs 114 to light in a pattern unique to the type of the surface 102.

First, the apparatus 10 identifies the type of the surface 102 by capturing and analyzing one or more images of the surface in a manner similar to that discussed above in conjunction with FIGS. 1-4B. For example, if the navigation device 100 is disposed on a carpet, then the carpet surface may generate an image (as captured by the device 22 of FIG. 1) similar to image 70 of FIG. 4A and having a histogram similar to the histogram 72 of FIG. 4B. Similarly, if the navigation device 100 is disposed on a desktop (which has a smooth, shiny surface), then the desktop surface may generate an image similar to the image 50 of FIG. 2A and having a histogram similar to the histogram 52 of FIG. 2B.

Next, the controller 116 adjusts one or more predetermined navigation device settings according to the type of the surface 102 identified by the apparatus 10. For example, if the apparatus 10 identifies the surface 102 as smooth surface such as a desktop, then the controller 116 may light only the LEDs (e.g., 114a and 114d) in the top row of the array 112. Lighting the LEDs 114 in different patterns corresponding to the type of the surface 102 may increase operator enjoyment, and thus may give the navigation device 100 a competitive edge in the market place. Alternatively, the LEDs 114 may be different colors, and the controller 116 may light only certain colored LEDs for a particular type of surface 102. For example, suppose the LEDs (e.g, 114a and 114d) in the top row of the array 112 are red, the LEDs in the middle row are white, and the LEDs in the bottom row are blue. The controller 116 may light the red LEDs 114 when the surface 102 is smooth and shiny, the white LEDs when the surface is rough, and the blue LEDs when the surface is fibrous like the surface of a carpet.

Referring to FIGS. 1 and 6, the controller 116 may also tune predetermined settings pertaining to a cursor-control function of the navigation device 100. Like conventional computer navigation devices, the navigation device 100 moves a cursor on a computer screen (not shown in FIG. 6) in a direction and at a rate that are proportional to the direction and rate at which the operator moves the navigation device over the surface 102. The direction and rate compose a movement vector. As discussed in previously incorporated U.S. patent application Ser. Nos. 10/680,525 filed Oct. 6, 2003, and Ser. No. 10/977,720 filed Oct. 30, 2004, the image-capturing detector 22 captures a series of images of the surface 102 at relatively high speed, and the processor 24 calculates the movement vector by comparing these images to one another to track relative movement of image features. The transmitter 108 provides the movement vector to the computer, which uses the vector to move the cursor. The image-processing algorithm(s) that the processor 24 uses to calculate the movement vector may have settings that are adjustable according to the type of the surface 102. For example, where the type of the surface 102 causes the captured images to have a low contrast, then the controller 116 may cause the processor 24 to execute a contrast-enhancing algorithm on the pixels of a captured image before comparing the image to another image. This contrast enhancement may improve the speed and/or accuracy of the processor's calculation of the movement vector. Conversely, where the type of the surface 102 causes the captured images to have a high contrast, then the controller 116 may cause the processor 24 to execute a less complex image-to-image comparison algorithm. Executing a less complex algorithm may allow the navigation device 100 to consume less power, and thus may extend the life of the batteries (not shown) in a cordless navigation device.

Still referring to FIG. 6, other embodiments of the navigation device 100 are contemplated. For example, instead of controlling the pattern of lit LEDs 114 based on the type of the surface 102 identified by the apparatus 10, the controller 116 may cause piezoelectric sound generators (not shown) to generate different sounds based on the surface type. Furthermore, the navigation device 100 may omit the controller 116, and a computer (not shown in FIG. 6) to which the navigation device is coupled may perform the controller functions discussed above. In addition, the controller 116 may communicate with the computer over a cable, and thus the transmitter 108 may be omitted. Moreover, the functions of the controller 116 may be performed by the processor 24 of the apparatus 10, or the functions of the processor 24 may be performed by the controller 116. Furthermore, although six LEDs 114 are shown, the navigation device 100 may include more or fewer than six LEDs.

Figure 7:
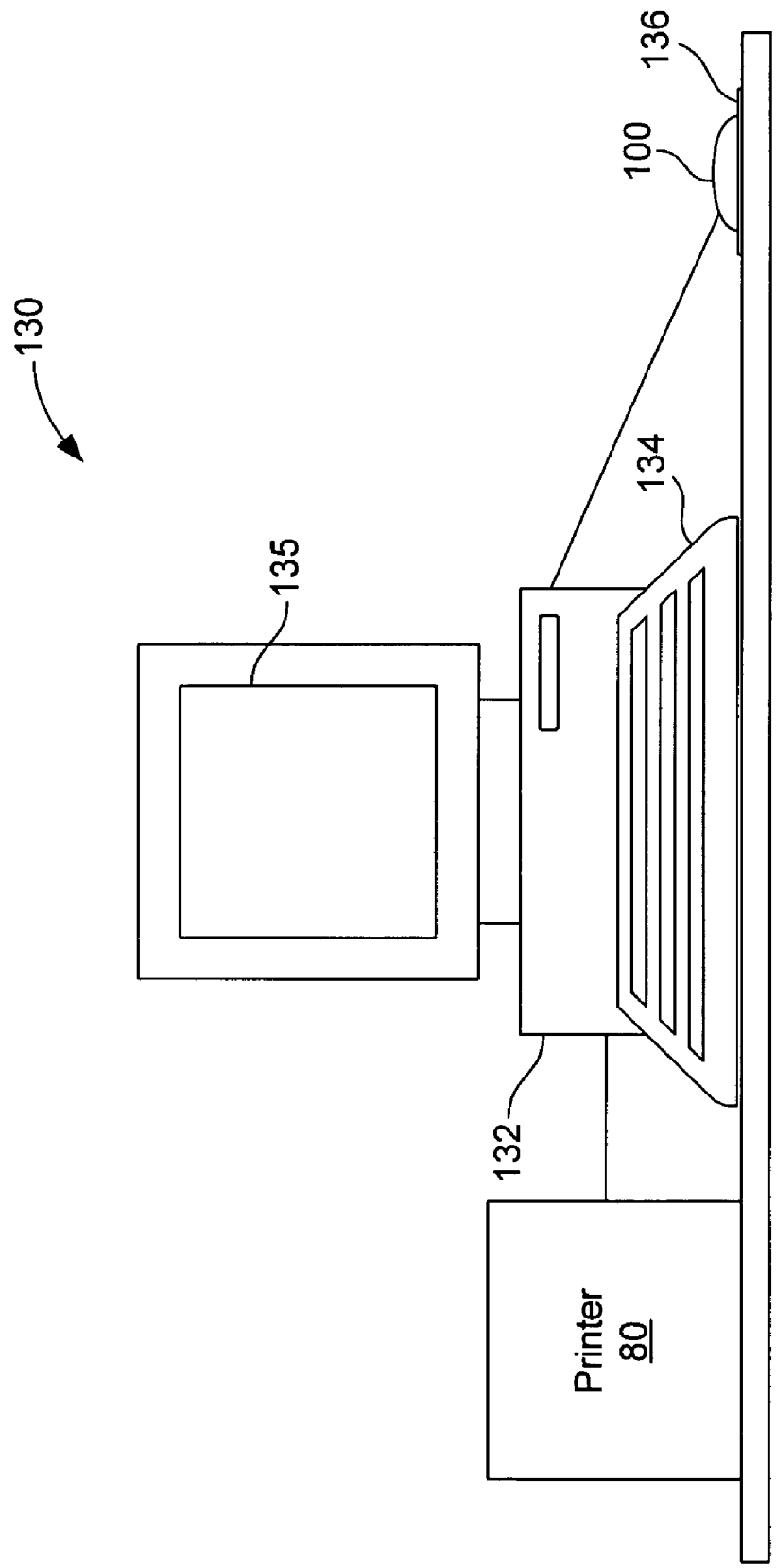
FIG. 7 is a diagram of a computer system that includes the printer of FIG. 5, the computer navigation device of FIG. 6, or both the printer and the computer navigation device according to an embodiment of the invention.

FIG. 7 is an isometric view of a computer system 130 that incorporates the printer 80 of FIG. 5, the computer navigation device 100 of FIG. 6, or both the printer and navigation device according to an embodiment of the invention.

In addition to the printer 80 and/or the navigation device 100, the system 130 includes a computer 132, a keyboard 134 for entering data into the computer, a display screen 135 for displaying data and a cursor (not shown) generated by the computer, and a mouse pad 136 on which the navigation device is disposed. The printer 80 can print electronic documents stored on the computer 132 as discussed above in conjunction with FIG. 5, and the navigation device 100 can move the cursor and generate operator-perceivable patterns or other novelty features that correspond to the type of surface on which the computer navigation device 100 is disposed.

From the foregoing it will be appreciated that, although specific embodiments of the invention have been described herein for purposes of illustration, various modifications may be made without deviating from the spirit and scope of the invention.

What is claimed is:

1. An apparatus, comprising:
   a detector operable to capture an image of a surface of a material;
   a processor coupled to the detector and operable to classify the material by analyzing the image;
   a beam source operable to direct a beam of electromagnetic energy onto the surface;
   wherein the detector is operable to capture the image by receiving a portion of the beam reflected from the surface;
   a housing operable to navigate the surface;
   wherein the detector is disposed in the housing; and
   wherein the processor is disposed in the housing and is operable to generate movement information in response to images of the surface that are captured by the detector and to identify a type of the surface by analyzing the image;
   wherein the processor is configured to tune a predetermined settings pertaining to a cursor-control function of the apparatus in response to the type of surface.

2. The apparatus of claim 1 wherein the detector is selected from a group comprising a CMOS imager and an integrated pixel array.

3. The apparatus of claim 1 wherein the beam source is selected from a group including a laser, a vertical-cavity surface-emitting laser, and an LED.

4. The apparatus of claim 1, further comprising:
   a beam source operable to direct a light beam onto the surface; and
   wherein the image comprises a pattern generated by a portion of the light beam reflected from the surface to the detector, the pattern selected from a group including a speckle pattern, a pattern comprising a picture of the surface, and a diffraction pattern.

5. The apparatus of claim 1 wherein:
   the processor is operable to analyze the image by determining a characteristic of the image; and
   the processor is operable to classify the material by comparing the determined characteristic to a predetermined characteristic that corresponds to the material.

6. The apparatus of claim 1 wherein:
   the processor is operable to analyze the image by generating an analysis of the image, the analysis being selected from a group including a histogram analysis, a spatial-frequency analysis, and a threshold analysis that compares a pixel or a sum of pixels to a predetermined threshold; and
   the processor is operable to classify the material by comparing the analysis of the image to a predetermined analysis that corresponds to the material.

7. The computer peripheral device of claim 1, further comprising:
   a first light source;
   a second light source; and
   wherein the processor is operable to activate the first light source in response to the surface being of a first type, and is operable to activate the second light source in response to the surface being of a second type.

8. The computer peripheral device of claim 1, further comprising:
   a laser operable to direct a laser beam onto the surface; and
   wherein the first image comprises a pattern generated by a portion of the laser beam reflected from the surface to the first detector.

9. A computer peripheral device, comprising:
   a first detector operable to capture a first image of a surface of a material;
   a processor coupled to the detector and operable to classify the material by analyzing the first image;
   wherein the material comprises a first medium having the surface;
   a first receptacle operable to receive the first medium;
   wherein the processor is operable to identify a type of the first medium by analyzing the first image; and
   a print mechanism operable to impart a printing agent onto the first medium according to a predetermined setting;
   wherein the processor is operable to adjust the predetermined setting according to the identified type of the first medium.

10. The computer peripheral device of claim 9 wherein:
    the first receptacle comprises a tray; and the first detector is operable to capture the first image while the medium is disposed in the tray.

11. The computer peripheral device of claim 9 wherein:
the first receptacle comprises a printing pathway; and
the first detector is operable to capture the first image while the medium is disposed in the printing pathway.

12. The computer peripheral device of claim 9 wherein the medium comprises paper.

13. The computer peripheral device of claim 9 further comprising:
a second receptacle operable to receive a second medium having a surface;
a second detector operable to capture a second image of the surface of the second print medium; and
wherein the processor is operable to identify the type of the second medium by analyzing the second image.

14. A computer system, comprising:
a computer peripheral device including, a beam source operable to direct a beam of electromagnetic energy onto a surface of a material and a detector operable to capture an image of the surface of the material; and
a processor coupled to the detector and operable to classify the material by analyzing the image;
wherein the computer peripheral device comprises an optical navigation device and wherein the surface is a navigation surface on which the optical navigation device is disposed:
wherein the processor is configured to tune predetermined settings pertaining to a cursor-control function of the optical navigation device in response to the classification of the material.

* * * * *

UNITED STATES PATENT AND TRADEMARK OFFICE
CERTIFICATE OF CORRECTION

PATENT NO. : 7,583,821 B2  
APPLICATION NO. : 11/019603  
DATED : September 1, 2009  
INVENTOR(S) : Tong Xie et al.

It is certified that error appears in the above-identified patent and that said Letters Patent is hereby corrected as shown below:

Column 11, Line 9, Claim 13, after "claim 9" insert --,--.

Column 12, Line 11, Claim 14, delete "disposed:" and insert --disposed;--.

Signed and Sealed this
Twenty-fifth Day of September, 2012

David J. Kappos
*Director of the United States Patent and Trademark Office*